United States Patent
Richardson et al.

(10) Patent No.: US 11,529,288 B2
(45) Date of Patent: Dec. 20, 2022

(54) INTEGRATED CAP AND SEAL SYSTEM

(71) Applicant: TTP Plc, Royston (GB)

(72) Inventors: Will Richardson, Stainland (GB); Santiago Ruiz-Valdepenas, Royston (GB); Daniel Strange, Royston (GB); Francisco Huhn, Royston (GB)

(73) Assignee: TTP plc., Royston (GB)

( * ) Notice: Subject to any disclaimer, the term of this patent is extended or adjusted under 35 U.S.C. 154(b) by 113 days.

(21) Appl. No.: 16/310,190

(22) PCT Filed: Jun. 12, 2017

(86) PCT No.: PCT/GB2017/051703
§ 371 (c)(1),
(2) Date: Dec. 14, 2018

(87) PCT Pub. No.: WO2017/216530
PCT Pub. Date: Dec. 21, 2017

(65) Prior Publication Data
US 2019/0192382 A1    Jun. 27, 2019

(30) Foreign Application Priority Data
Jun. 15, 2016 (GB) .................... 1610368

(51) Int. Cl.
*A61J 1/14*    (2006.01)
*A61J 1/20*    (2006.01)
(Continued)

(52) U.S. Cl.
CPC ....... *A61J 1/1425* (2015.05); *A61B 5/150572* (2013.01); *A61J 1/1406* (2013.01);
(Continued)

(58) Field of Classification Search
CPC ...... A61J 1/2096; A61J 1/1425; A61J 1/1406; B65D 51/002; A61B 5/150572
(Continued)

(56) References Cited

U.S. PATENT DOCUMENTS 4,084,718 A    4/1978  Wadsworth
4,516,967 A *  5/1985  Kopfer .................. A61J 1/2096
                                                    604/87
(Continued)

FOREIGN PATENT DOCUMENTS

EP    3 006 063 A1    4/2016
JP    10151171 A      6/1998
(Continued)

OTHER PUBLICATIONS

International Search Report dated Aug. 10, 2017, in International Application No. PCT/GB2017/051703; Filed: Jun. 12, 2017; Applicant: TTP PLC.
(Continued)

*Primary Examiner* — Timothy P. Kelly
(74) *Attorney, Agent, or Firm* — Erise IP, P.A.

(57) ABSTRACT

A cap and seal system for a liquid medicament container. The system comprises a cap formed from a substantially rigid material, and has a retention component integrally formed therewith. A seal is formed from a material which is less hard than the cap and positioned within the cap such that, when the retaining component retains the cap on a container in use the seal is positioned such that it forms a fluid tight seal between the cap and the container. A recess is formed in the seal through which a liquid outlet channel can pass in use to access the contents of the container via the cap and the seal.

13 Claims, 3 Drawing Sheets

(51) Int. Cl.
  *B65D 51/00* (2006.01)
  *A61B 5/15* (2006.01)
(52) U.S. Cl.
  CPC .............. *A61J 1/201* (2015.05); *A61J 1/2096* (2013.01); *B65D 51/002* (2013.01); *A61B 5/15003* (2013.01); *A61B 5/150351* (2013.01); *A61J 1/1487* (2015.05)
(58) Field of Classification Search
  USPC .................................................. 215/247, 249
  See application file for complete search history.

(56) References Cited

U.S. PATENT DOCUMENTS

| | | | | |
|---|---|---|---|---|
| 5,297,599 | A | * | 3/1994 | Bucheli .............. G01N 35/1002 141/330 |
| 5,433,330 | A | * | 7/1995 | Yatsko ................ B65D 51/002 215/247 |
| 5,738,233 | A | * | 4/1998 | Burns ................. B01L 3/50825 215/249 |
| 5,895,383 | A | | 4/1999 | Niedospial, Jr. |
| 8,122,923 | B2 | * | 2/2012 | Kraus ....................... A61J 1/22 |
| 2002/0095121 | A1 | * | 7/2002 | Norton ................... A61J 1/2096 604/187 |
| 2010/0024914 | A1 | * | 2/2010 | Baker ................... B65D 51/002 141/27 |
| 2010/0089862 | A1 | * | 4/2010 | Schmitt ................ B65D 51/241 215/249 |
| 2012/0248057 | A1 | * | 10/2012 | Bogle .................. B65D 51/002 215/43 |
| 2015/0013837 | A1 | * | 1/2015 | Barrelle ................ A61J 1/2082 141/89 |

FOREIGN PATENT DOCUMENTS

| | | |
|---|---|---|
| WO | 2013/047030 A1 | 4/2013 |
| WO | 2014/169081 A2 | 10/2014 |

OTHER PUBLICATIONS

Written Opinion of the International Searching Authority dated Aug. 10, 2017, in International Application No. PCT/GB2017/051703; Filed: Jun. 12, 2017; Applicant: TTP PLC.
European Examination Report dated Sep. 1, 2020; Application No. 17 730 559.6; Applicant: TTP PLC.

* cited by examiner

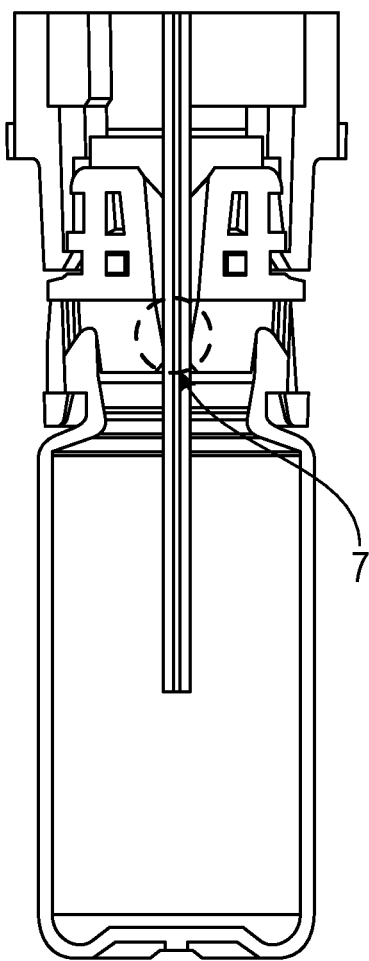
FIG. 4
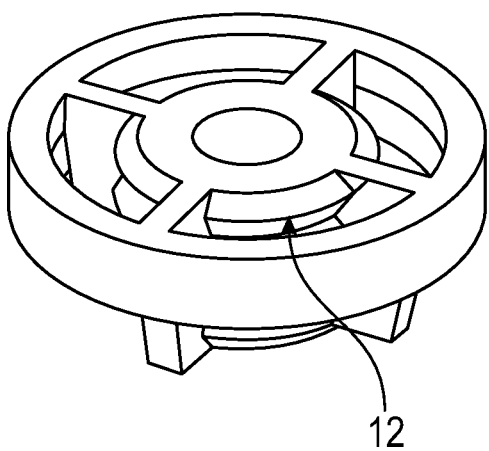 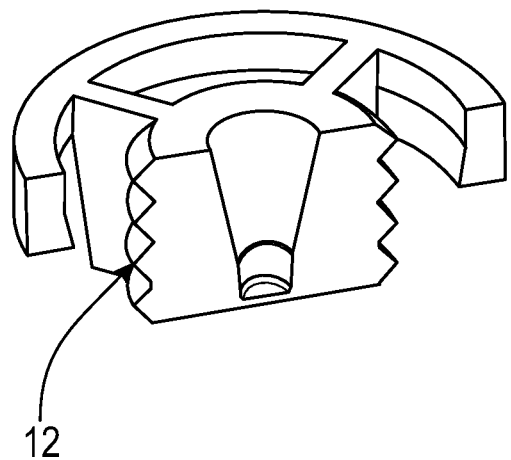
FIG. 5  FIG. 6

INTEGRATED CAP AND SEAL SYSTEM

RELATED APPLICATIONS

The present application is a national stage application under 35 U.S.C. § 371 of International Application No. PCT/GB2017/051703, filed 12 Jun. 2017, which claims priority to Great Britain Patent Application No. 1610368.1, filed 15 Jun. 2016. The above referenced applications are hereby incorporated by reference into the present application in their entirety.

FIELD

The present invention relates generally to a cap and seal system for drug delivery systems with a separate dose container. In particular to such a system for use with a liquid medicament container into which an outlet channel is inserted in use.

BACKGROUND

Drug delivery devices with separate dose containers are designed to have a long product-life. The dose container part of such systems is then used as the replaceable component. The separate dose container contains a liquid medicament, such as a liquid drug, solution suspension or colloid, whose sterility and stability must be maintained through its shelf life. However, it must be able to interface and create a robust seal with the drug delivery device through its use life. Furthermore, being replaceable, the dose container should also be inexpensive. Typically, such a container is composed of a bottle and a cap, the latter interfacing with the drug delivery device. Hence, the cap must meet certain criteria, such as: no fluid exchange being allowed before the outlet channel (e.g.: needle, piston, etc.) is inserted; maintenance of a tight and leak-free seal with the outlet channel; and maintenance of a tight and leak-free seal with the container.

At present such criteria are attempted to be met by septum seals or moulded caps, but these have disadvantages. Septum seals are rubber stoppers that give an air-tight seal. They are solid and initially have no ports (e.g.: holes) through which the liquid medicament can exit. In order to be able to let liquid flow out, the septum must be pierced, which either requires a sharp needle, a significant user force, or both. A sharp needle reduces user safety. On the other hand, a significant force is hard to produce, which is uncomfortable to the user and may be impossible for people with physical impairments. Furthermore, the simple piercing of the septum might not result in a perfect seal. Moulded caps are able to achieve an air-tight steal, when used in conjunction with o-rings and/or gaskets. As no part is pierced through, the operating force is much lower than with septum seals. However, multiple parts are required, requiring additional assembly. Furthermore, die cut gaskets have high tolerances. An alternative would be to mould the gaskets, but in this case the tolerances of each individual part add up, resulting in less control of manufacturing tolerances and increased expense in manufacture.

Alternatives to simply piercing a septum are disclosed in EP0499481 and WO0057835. Such devices present a "needle" like feature. The device attaches to the container and pierces the septum. The outlet channel is then inserted through/in the device. The inherent problems to piercing a septum, such as sharp features, remain.

An improvement on the septum seal is disclosed in U.S. Pat. No. 4,084,718, where the septum is incorporated in the cap, rather than the container. However, such an invention is composed of multiple parts and still requires the piercing, potentially with a sharp needle, of a fairly thick septum.

EP0088056 does not require a septum, rather relying on compliance between the outlet channel and the container neck. However, obtaining such a seal with a rigid material requires a rather large compression force. If on the other hand, a softer material is used for the container (better compliance with the outlet channel), then barrier properties (e.g.: water/moisture, oxygen, etc.) are sacrificed. The device is also designed to contain a single dose, which is not suitable for a variety of drug delivery devices.

Moreover, most of these devices have no feature for permanent attachment of the outlet channel to the container.

Accordingly it will be appreciated that there is a need for a low cost one-part cap and sealing system to create an air-tight seal with the delivery device, without requiring significant user force.

SUMMARY

According to the present invention there is provided a cap and seal system for a liquid medicament container, the system comprising a cap formed from a substantially rigid material and having a retention component integrally formed therewith; and a seal formed from a material which is less hard than the cap and positioned within the cap such that, when the retaining component retains the cap on a container in use the seal is positioned such that it forms a fluid tight seal between the cap and the container; and a recess formed in the seal through which a liquid outlet channel can pass in use to access the contents of the container via the cap and the seal.

The present invention provides an arrangement in which a low cost cap and sealing arrangement can be provided which is fluid-tight, simple to attach to a container, and yet which can easily allow access to the contents of a container by simple low-force insertion of an access channel.

DESCRIPTION OF THE DRAWING FIGURES

Examples of the present invention will now be described with reference to the accompanying drawings, in which:

FIG. 4 is a side cross-sectional view of the cap and seal system of FIGS. 1 and 2 attached to a container and with a liquid channel inserted; and FIGS. 5 & 6 are perspective and perspective cross-sectional views of an alternative seal assembly.

DETAILED DESCRIPTION

Figure 1:
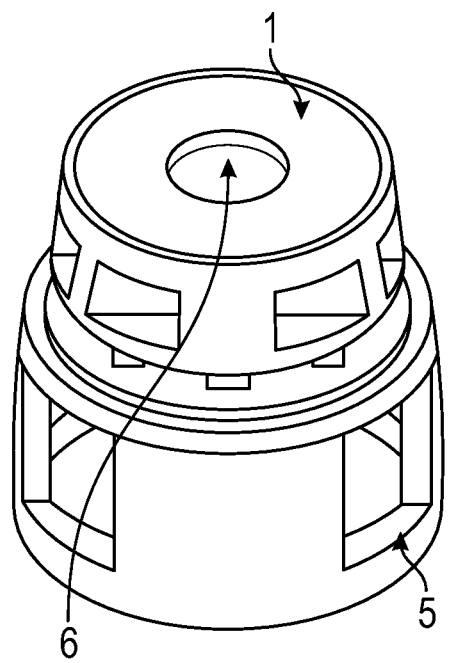
FIG. 1 is a perspective view from above of a cap and seal system according to the present invention.
Figure 2:
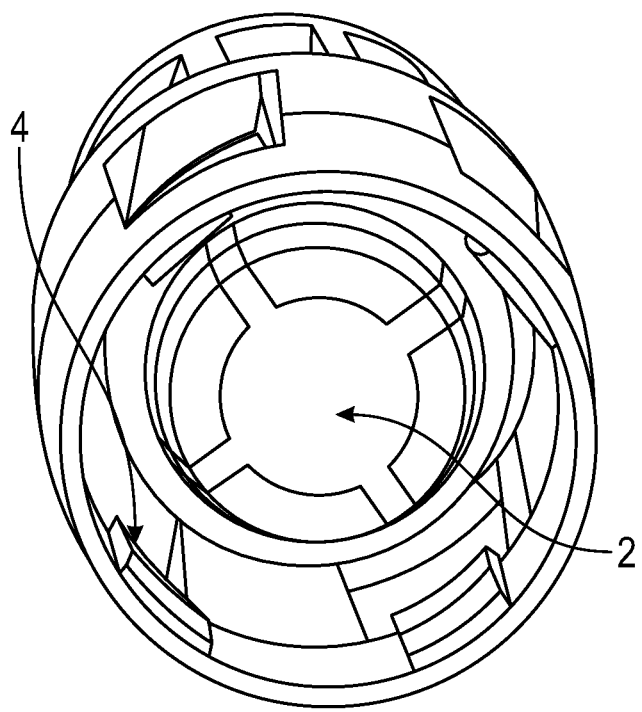
FIG. 2 is a perspective view from below of a cap and seal system according to the present invention.

Referring to FIGS. 1 and 2, the system of the present invention has two main elements, a cap 1 and a seal 2. The cap 1 is, for example, a polymer structure and the seal 2 may be made of an elastomer. However, these are not the only possible combination of materials. Generally, the cap 1 should be made of a relatively hard material, since it must be able to withstand loading forces from interaction with a medical device or other external component, without substantially changing shape or creeping. On the other hand, the seal 2 should be made of a softer and pliable material, since it creates a tight seal by complying to an outlet channel's outside surface in use. Ideally, both materials should be inexpensive to reduce the overall cost. Both parts can be co-moulded, with the latter being moulded inside the former. Co-moulding has the benefit that, since the two parts are effectively created as one, everything is done in one moulding process step. A further advantage of co-moulding is that no assembly is required and there is no need for other parts, such as o-rings or gaskets. Furthermore, because the seal 2 is moulded against/inside the cap 1, the individual tolerances are defined solely by any moulding tool, resulting in better control of those tolerances.

The cap 1 and seal 2 can each be manufactured independently or in combination using a moulding process adapted according to the material selection. Known moulding techniques that are suitable for production of these components include vacuum forming, thermoplastic or metal injection moulding, thermosetting injection, compression moulding and transfer moulding. Either or both of the cap 1 and/or seal 2 could alternatively be produced using additive manufacturing techniques such as Fused Deposition Modelling, Fused Filament Fabrication, Stereolithography, Selective Laser Sintering or other 3D additive manufacturing processes. A wide variety of materials, including thermoplastics, photopolymers, wax, polycarbonate, and even metals, such as aluminium, titanium and nickel, or ceramics may be deployed using these manufacturing methods.

FIG. 1 shows an example of the cap 1 that can be produced by moulding. The lower part of the cap 1 is constructed so as to interface with a container 3, in this case a bottle, by housing the neck. As shown in FIG. 2, the cap 1 is shaped to provide seating for the seal 2, which may be contained inside the lower region of the cap 1, against the lower surface of the upper region of the cap 1. The cap 1 can be manufactured by moulding, or by additive manufacturing as described earlier. If required, the seal 2 may be produced by the same or by a separate manufacturing step or process. As further shown in FIG. 2, the region of the cap 1 around the seal 2 seating contains internal snap features 4 that keep the container 3 attached to the cap 1 in use. It may, as shown, also feature windows 5 for seal moulding.

Figure 3:
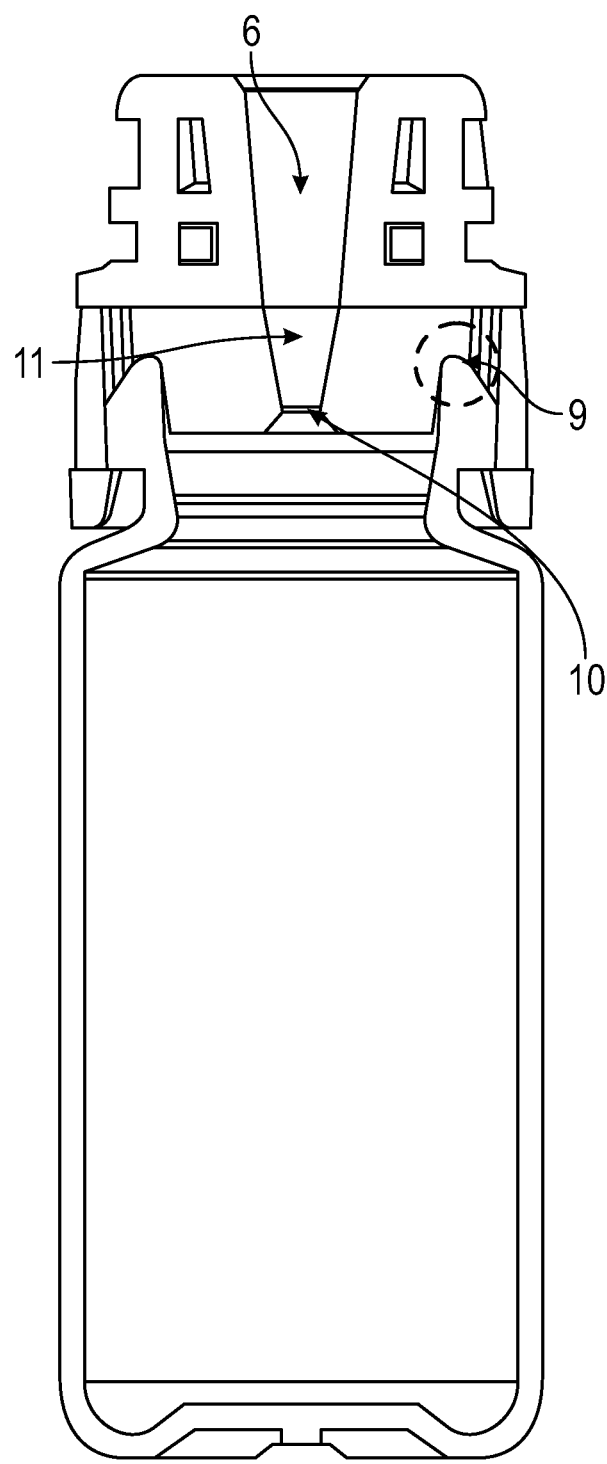
FIG. 3 is a side cross-sectional view of the cap and seal system of FIGS. 1 and 2 attached to a container.

FIG. 1 further shows that the upper region of the cap features an internal hole 6 through which an outlet channel 7 can be inserted. The internal hole's cross section may vary along its axis, in order to better suit the geometry of the outlet channel 7 and/or guide the outlet channel through the hole 6. For example, the tapered profile illustrated in FIG. 3 allows for insertion guidance, while minimising scraping because of the high steepness. This tapering may be a linear taper, a curved taper or comprise a compound shaped taper to optimally provide the function of guiding the outlet channel 7 into, and through, the cap hole 6. Externally, the cap 1 may contain any number of features to help with the delivery system operation, such as grooves 8 to interface with a moving piston or other parts. A further seal (not shown) can be formed over the top surface of the cap 1 and cap hole 6 in order to isolate and therefore protect the medicament, for example from moisture and air ingress and maintaining its sterility and stability before it is used. Such a seal may be formed by applying a foil or film coating over the upper surface of the upper cap.

The seal part 2 resides within the cap structure 1. It functions to provide a secure seal 9 with the medicament bottle once the cap 1 has been snapped into place. The seal additionally functions to create a tight and leak-free seal with the outlet channel 7, when inserted. Advantageously, the seal 2 may be co-moulded with the cap 1, avoiding the need for assembly as well as providing benefits with regard to manufacturing tolerances. However, the seal component 2 can be manufactured in a separate step or process to that used for production of the cap 1. Such a situation may be beneficial if the materials selected for each component have significantly different properties.

The seal with the outlet channel 7 when it is inserted is achieved by squeezing the walls of the internal hole 11. Before the outlet channel 7 is inserted, the minimum distance between these walls, that is the diameter of the hole 11, is smaller than the outlet channel 7 outside diameter. After the outlet channel 7 is inserted, the distance between the walls is equal to the outside diameter of the outlet channel 7. The normal stress resulting from the compression of the walls creates a tight and leak-free seal with the outside surface of the outlet channel 7. As mentioned above, the internal hole cross section may vary along its axis, in order to better suit the geometry of the outlet channel 7 and/or guide the outlet channel 7 through the hole 11.

The seal 9 with the container 3 is achieved via compression of an upper surface of the container 3 against the seal's outside lower surface. In a case with no container 3 inserted, the distance between the upper surface of the snap features of the cap structure and the seal's outside lower surface is smaller than the distance between the corresponding surfaces of the neck of the container 3. When the container 3 is inserted, the neck and the seal are compressed, generating a contact force, which effectively seals the container in a fluid tight manner.

Optionally, but advantageously, the seal hole may feature a thin septum barrier 10 with the objective of having a further protection layer for the liquid medicament. This barrier 10 is broken during insertion of the liquid outlet channel 7, preferably requiring a minimal amount of additional force. Whereas a common septum seal is bulky, large and fairly thick, the septum barrier 10 here can be very small and thin, which does not significantly increase the piercing force and therefore allows the use of a blunt outlet channel such as a capillary, dip or other tube as well as other alternatives such as needles and other sharpened outlet channels. Furthermore, the seal with the outlet channel 7 is defined by the geometry of the seal hole 11 and not the geometry of any gap that is created, and hence will not be affected by the variability inherent in piercing.

In combination, the above described cap 1 and seal 2 structures provide a number of advantages for use with a medicament container 3, such as a bottle. Each component may be manufactured independently using processes that are optimised for the selection of each specific material. The cap 1 must be strong enough to provide a sufficiently rugged interface with the mechanical instrument into which the medicament container 3 will be inserted. Suitable materials are polymers, thermoplastics and even metals. On the other hand, the seal 2 must be soft and pliable enough to form a compliant seal with the outer surface of the outlet channel 7. The seal 2 might readily be formed using a moulding process, whereas the cap might be best manufactured using an additive manufacturing process or a different moulding process.

Advantageously, however, the choice of materials will be made such that both cap 1 and seal 2 may be co-moulded, such as polypropylene for the cap 1 and a thermoplastic elastomer for the seal 2. Due to its lower cost, this method is very advantageous for large-scale production. Alternatively, the choice may be made such that both the cap 1 and seal 2 may be produced using additive manufacturing techniques.

The structure of the combined cap 1 and seal 2 is such that the internal snap features 4 of the cap 1 form a secure mounting to the container 3, whilst the soft and pliant seal 2 forms a seal once the cap 1 and seal 2 combination has been snapped into place.

When thus assembled, any external seal over the cap hole 6 is pierced, typically by insertion of the outlet channel 7, the cap hole 6 guides the outlet channel 7 into and through the cap 1. When combined with the seal 2, the outlet channel 7 is thus guided into the seal hole 11, requiring some increased frictional force resulting from the seal hole diameter being smaller than the outlet channel external diameter. The combination of seal 2 and narrower seal hole diameter provide protection such that a thin septum barrier 10 can be incorporated within or, at the top or bottom edge of, the seal hole 11 to provide a further level of protection for the medicament inside the container 3. This thin septum barrier 10 may alternatively be formed directly over the surface of the container 3, such that it abuts the base of the seal hole 11 when the cap 1 and seal 2 combination is snapped into position.

As stated above, a preferred embodiment features a co-moulded cap 1 and seal 2 for use with a medicament container 3 comprising a single chamber. As also described above the cap 1 and seal 2 may be manufactured independently using any known manufacturing technique and then assembled. For example, FIGS. 5 and 6 show a seal 2 that is moulded separately from the cap (not shown). This particular embodiment presents snap features 12, in order to join the two parts.

They are assembled by pushing the seal 2 into the cap, where the seal's snaps fit with snaps in the cap. Some medicaments may optimally be delivered using multiple chambers, for example a concentrated active compound which is mixed at the time of dispensing with a liquid solvent or base medium. A multi-chambered container can thus be used with the techniques described herein, having a cap with two (or more) holes for discrete outlet channels, one per chamber, and associated seal structure or structures aligned with the cap holes and optimised for the respective outlet channels associated with each chamber. Application of a thin septum seal layer over the top of each chamber can prevent cross contamination during assembly of the container, cap and seal combination.

The invention claimed is:

1. A cap and seal system for a liquid medicament container, the system comprising:
   a cap formed from a substantially rigid material and having a retainer integrally formed therewith, wherein an upper region of the cap comprises an internal hole into which a liquid outlet channel is inserted; and
   a seal formed from a material which is less hard than the cap and positioned within a lower region of the cap such that, when the retainer retains the cap on a container in use the seal forms a fluid tight seal between the cap and the container; and
   a seal hole formed in the seal through which the liquid outlet channel passes in use to access the contents of the container via the cap and the seal;
   wherein the seal hole in the seal has a cross-sectional area which narrows in the direction of insertion of the liquid outlet channel,
   wherein the internal hole has a cross section which is tapered along its axis to conform to a geometry of the liquid outlet channel, and
   wherein the internal hole and the seal hole are in vertical alignment with each other such that the internal hole is located above the seal hole.

2. The system according to claim 1, wherein the cap and seal are arranged such that they are co-moulded in a single production step.

3. The system according to claim 1, wherein the vertical alignment of the internal hole above the seal hole guides the insertion of the liquid outlet channel through the internal hole in the cap and into the seal hole.

4. The system according to claim 3, wherein the recess seal hole has a breakable septum formed therein.

5. The system according to claim 1, wherein the retainer is one or more snap-fit components arranged to snap-fit onto a neck of the container in use.

6. The system according to claim 1, wherein the cap has windows formed on its exterior surface.

7. The system according to claim 6, wherein the cap has an interface formed thereon for interfacing with a piston for driving the outlet channel in use.

8. A cap and seal system for a liquid medicament container, the system comprising:
   a cap formed from a substantially rigid material and having a snap component integrally formed therewith, wherein an upper region of the cap comprises an internal hole into which a liquid outlet channel is inserted; and
   a seal formed from a material which is less hard than the cap and positioned within a lower region of the cap such that, when the snap component retains the cap on a container in use the seal forms a fluid tight seal between the cap and the container; and
   a seal hole formed in the seal through which the liquid outlet channel passes in use to access the contents of the container via the cap and the seal;
   wherein the seal hole in the seal has a cross-sectional area which narrows in the direction of insertion of the liquid outlet channel,
   wherein the internal hole has a cross section which is tapered along its axis to conform to a geometry of the liquid outlet channel, and
   wherein the internal hole and the seal hole are in vertical alignment with each other such that the internal hole is located above the seal hole.

9. The system according to claim 8, wherein the cap and seal are arranged such that they are co-moulded in a single production step.

10. The system according to claim 8, wherein the vertical alignment of the internal hole above the seal hole guides the insertion of the liquid outlet channel through the internal hole in the cap and into the seal hole.

11. The system according to claim 10, wherein the seal hole has a breakable septum formed therein.

12. The system according to claim 8, wherein the snap component is one or more snap-fit components arranged to snap-fit onto a neck of the container in use.

13. The system according to claim 8, wherein the cap has windows formed on its exterior surface.

* * * * *